United States Patent [19]

Onodera

[11] Patent Number: 5,127,531
[45] Date of Patent: Jul. 7, 1992

[54] FLUID SAMPLE TUBE STAND WITH HOLDER SUPPORT MECHANISM

[75] Inventor: Tsuneyoshi Onodera, Yamanashi, Japan

[73] Assignee: Terumo Kabushiki Kaisha, Tokyo, Japan

[21] Appl. No.: 651,453

[22] Filed: Feb. 5, 1991

Related U.S. Application Data

[63] Continuation-in-part of Ser. No. 524,168, May 15, 1990, abandoned.

[30] Foreign Application Priority Data

May 19, 1989 [JP] Japan .................................. 1-126306
Mar. 22, 1990 [JP] Japan .................................. 2-72735

[51] Int. Cl.⁵ .......................................... A47B 73/00
[52] U.S. Cl. ................................ 211/74; 206/446; 248/146
[58] Field of Search ................ 248/311.2, 146, 312, 248/312.1, 316.8; 211/74; 422/104, 99; 206/446, 443, 571; 604/259, 257

[56] References Cited

U.S. PATENT DOCUMENTS

| | | | |
|---|---|---|---|
| 1,222,486 | 4/1917 | Swanson | 211/74 X |
| 2,046,864 | 7/1936 | Baker . | |
| 2,650,702 | 9/1953 | Shanahan | 206/446 X |
| 2,741,913 | 4/1956 | Dovas | 211/74 X |
| 2,906,479 | 9/1959 | Strachan | 248/311.2 X |
| 3,029,934 | 4/1962 | Hennessey | 206/446 X |
| 3,217,891 | 11/1965 | Weaver | 211/74 X |
| 3,640,437 | 2/1972 | Galy . | |
| 3,860,048 | 1/1975 | White | 211/74 X |
| 3,863,809 | 2/1975 | Christine et al. | 248/311.2 X |
| 3,893,569 | 7/1975 | Hoch | 211/74 |
| 4,055,396 | 10/1977 | Meyer et al. | 248/311.2 X |
| 4,057,148 | 11/1977 | Meyer et al. | 206/443 X |
| 4,240,547 | 12/1980 | Taylor | 206/443 X |
| 4,572,365 | 2/1986 | Bruno et al. | 206/443 X |
| 4,681,219 | 7/1987 | Kitchens | 211/74 X |
| 4,932,533 | 6/1990 | Collier | 211/74 X |
| 4,943,111 | 7/1990 | Van der Caan | 248/311.2 X |

*Primary Examiner*—Carl D. Friedman
*Assistant Examiner*—Korie H. Chan
*Attorney, Agent, or Firm*—Frishauf, Holtz, Goodman & Woodward

[57] ABSTRACT

A fluid sample tube stand includes a stand block for vertically holding a plurality of fluid sample tubes such as blood sample tubes, and a holder support mechanism mounted on the stand block, for supporting a holder which can hold one, at a time, of the fluid sample tubes. The holder support mechanism has a pair of support arms coupled to the stand block, for holding a flange of the holder, and a horizontal support member integral with the support arms, the horizontal support member having a cavity for insertion of the flange therein. The holder support mechanism is detachably mounted on the stand block.

12 Claims, 9 Drawing Sheets

FLUID SAMPLE TUBE STAND WITH HOLDER SUPPORT MECHANISM

This application is a continuation-in-part of prior application Ser. No. 07/524,168, filed May 15, 1990, now abandoned.

BACKGROUND OF THE INVENTION

The present invention relates to a fluid sample tube stand having a holder support mechanism for vertically supporting a holder in which a tube such as a fluid sample tube for containing a blood sample is inserted.

When blood samples are extracted from a blood vessel in a human body and stored in fluid sample tubes, these fluid sample tubes are held on a blood sample tube stand. One conventional blood sample tube stand is shown in FIGS. 1 and 2 of the accompanying drawings. The illustrated blood sample tube stand, generally denoted at 2, has a stand block 4 in the form of a substantially rectangular parallelepiped. The stand block 4 has a plurality of vertical cylindrical holes 8 defined therein and opening at an upper surface 6 of the stand block 4. The holes 8 vertically receive fluid sample tubes (blood sample tubes) which have hemispherical bottoms. The hoes 8 have open ends defines by tapered surfaces 8a for easy insertion of the blood sample tube into the hole 3.

The conventional blood sample tube stand 2 serves to only hold the blood sample tubes which contain blood samples, and does not perform any other functions. If a blood sample tube is mounted in a blood sample tube holder and a blood sample is to be introduced into the blood sample tube through a winged needle, then the blood sample tube holder has to be either manually gripped by the user or placed on a table or the like. When the blood sample is to be taken from a human arm, one of the hands of the user has to be occupied to hold the arm. After one blood sample tube is filled up with blood, another blood sample tube is inserted in the blood sample tube holder. If many data are to be obtained from the blood and there are many blood donors to extract blood samples from, then many blood sample tubes must be used to store the extracted blood samples. The above process for obtaining many blood samples and storing them in many blood sample tubes, using the conventional blood sample tube stand, is tedious and time-consuming.

SUMMARY OF THE INVENTION

It is a general object of the present invention to provide a fluid sample tube stand with a holder support mechanism which supports a fluid sample tube holder so that the user is not required to manually hold the fluid sample tube holder or place the fluid sample tube holder on a table, and hence the user can easily handle a fluid sampling instrument.

A major object of the present invention is to provide a fluid sample tube stand with a holder support mechanism which allows tubes such as blood sample tubes to be successively supported for sampling blood, the fluid sample tube stand being capable of holding the blood sample tubes vertically immediately after the blood samples have been collected.

Another object of the present invention is to provide a fluid sample tube stand with a holder support mechanism which permits a fluid sample tube to be easily transferred from the holder support mechanism reliably to the fluid sample tube stand.

Still another object of the present invention is to provide a fluid sample tube stand comprising a stand block for vertically holding a plurality of fluid sample tubes, and a holder support mechanism mounted on the stand block, for supporting a holder which can hold one, at a time, of the fluid sample tubes.

Yet another object of the present invention is to provide the fluid sample tube stand wherein the holder support mechanism has a pair of support arms coupled to the stand block, for holding a flange of the holder.

Yet still another object of the present invention is to provide the fluid sample tube stand wherein the holder support mechanism has a horizontal support member integral with the support arms the horizontal support member having a cavity for insertion of the flange therein.

A further object of the present invention is to provide the fluid sample tube stand wherein the horizontal support member has arcuate horizontal walls defining the cavity therebetween and having portions complementary in shape to the flange.

A still further object of the present invention is to provide the fluid sample tube stand wherein the support arms have on distal ends thereof respective slanted surfaces which are spread away from each other.

A yet further object of the present invention is to provide the fluid sample tube stand wherein the holder support mechanism is detachably mounted on the stand block.

A yet still further object of the present invention i to provide the fluid sample tube stand wherein the holder support mechanism includes a support plate held against the stand block and a step removably engaging the stand block, whereby the holder support mechanism is detachably mounted on the stand block.

The above and other objects, features and advantages of the present invention will become more apparent from the following description when taken in conjunction with the accompanying drawings in which a preferred embodiment of the present invention is shown by way of illustrative example.

DETAILED DESCRIPTION OF THE PREFERRED EMBODIMENT

Figure 1:
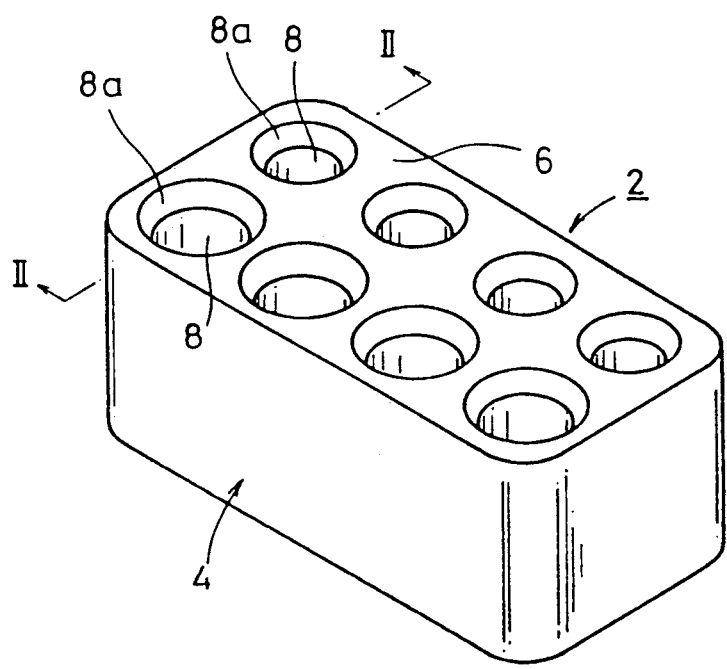
FIG. 1 is a perspective view of a conventional fluid sample tube stand.
Figure 2:
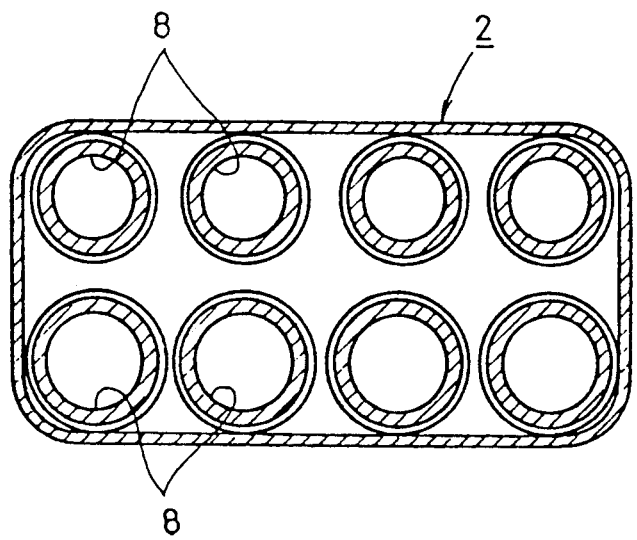
FIG. 2 is a cross-sectional view taken along line II—II of FIG. 1.
Figure 3:
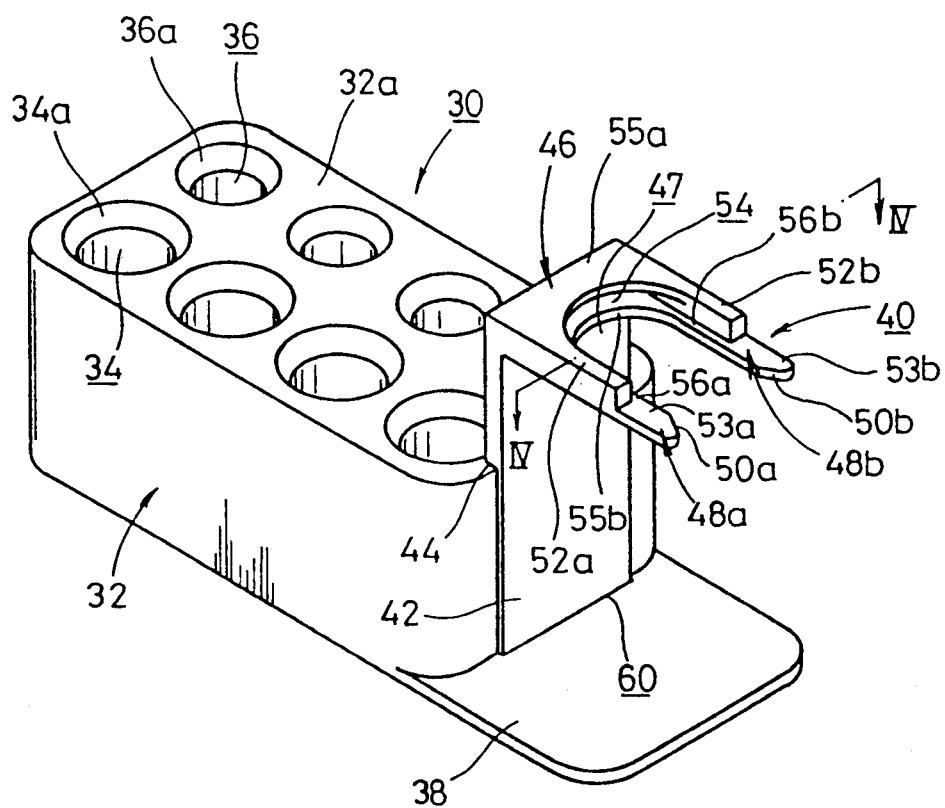
FIG. 3 is a perspective view of a fluid sample tube stand with a holder support mechanism according to the present invention.

FIG. 3 shows a fluid sample tube stand with a holder support mechanism according to the present invention. The fluid sample tube stand of the present invention will be described as being used to hold blood sample tubes. Therefore, the fluid sample tube stand will also be referred to as a blood sample tube stand.

The blood sample tube stand, generally denoted at 30, has a stand block 32 in the form of a hollow rectangular parallelepiped. The stand block 32 has a plurality of holes defined therein for vertically holding evacuated blood sample tubes. These holes include an array of four vertical holes 34 and an adjacent array of four vertical holes 36, the arrays of holes 34, 36 being parallel to each other. The holes 34, 36 have different diameters, and have upper open ends opening at an upper surface 32a of the stand block 32. The upper open ends of the holes 34, 36 are defined tapered surfaces 34a, 36a which are spread upwardly for easy insertion of the evacuated blood sample tubes which have hemispherical bottoms, into the holes 34, 36. The stand block 32 is preferably molded, as a unitary structure, of transparent or semitransparent synthetic resin.

Figure 4:
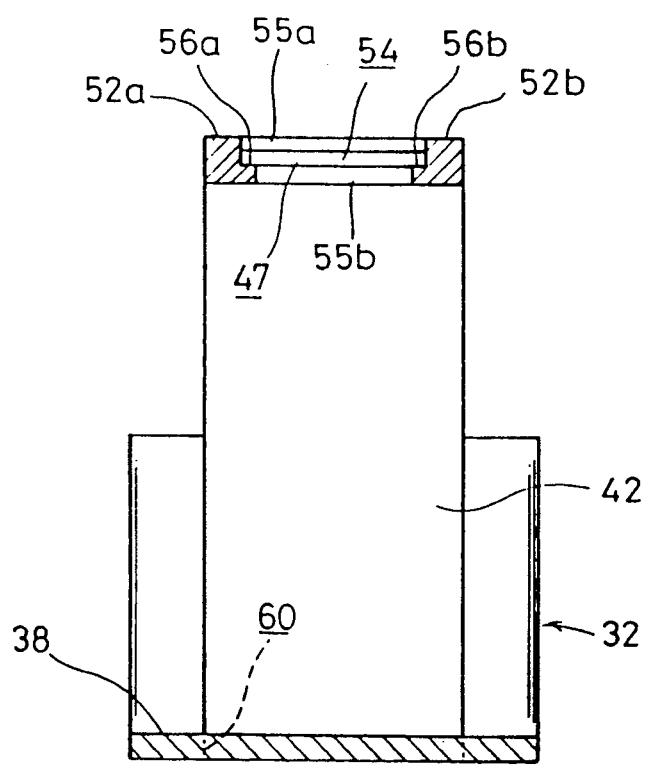
FIG. 4 is an enlarges cross-sectional view taken along line IV—IV of FIG. 3.

A plate 38 extends laterally from one side of the bottom of the stand block 32. A holder support mechanism 40 for supporting a blood sample tube holder 74 (FIG. 5) is mounted on the plate 38 and the stand block 32. The holder support mechanism 40 has a support plate 42 extending vertically upwardly toward the upper surface 32a of the stand block 32. The support plate 42 has a step 44 engaging an end of the upper surface 32a of the stand block 32 which has a side terminating at the support plate 42. Above the step 44, the support plate 42 has an increased thickness and extends further upwardly, terminating in a horizontal support member 46 extending substantially parallel to the plate 38 in overhanging relation thereto. The horizontal support member 46 is relatively thick and has a central recess 47 of a semielliptical shape, defining a pair of parallel support arms 48a, 48b spaced from each other. The support arms 48a, 48b comprise respective thicker portions 52a, 52b closer to the support plate 42 and thinner portions 53a, 53b remote from the support plate 42, with steps 56a, 56b defined therebetween (see also FIG. 4).

The thinner portions 53a, 53b have on distal ends thereof respective inner slanted surfaces 50a, 50b which are spread away from each other in a direction away from the recess 47 for easily insertion of a blood sample tube holder into the recess 47 between the support arms 48a, 48b.

The horizontal support member 46 has a cavity 54 defined therein in communication with the recess 47 and extending toward the support plate 42. Essentially, the cavity 54 is defined between upper and lower arcuate walls 55a, 55b of the horizontal support member 46.

The support plate 42 has a flat lower end removably engaging in a rectangular groove 60 defined in an upper surface of the plate 38 adjacent to the side of the stand block 32. Therefore, the holder support mechanism 40 can easily be coupled to the stand block 32 with the step 44 being held against the side edge of the stand block 32 and also with the lower end of the support plate 42 being inserted in the groove 60. Stated otherwise, the holder support mechanism 40 is removably combined with the stand block 32. Alternatively, the holder mechanism 40 may be integrally joined to the stand block 32.

The holder support mechanism 40 which is removably coupled to the stand block 32 offers certain advantages. After a blood sample is collected, only the holder support mechanism 40 can be removed from the stand block 32, and the stand block 32 with a plurality of vertically arranged blood sample tubes containing blood samples can be sent to an inspection process. The holder support mechanism 40 may be attached to another stand block 32 for collecting blood samples.

Figure 5:
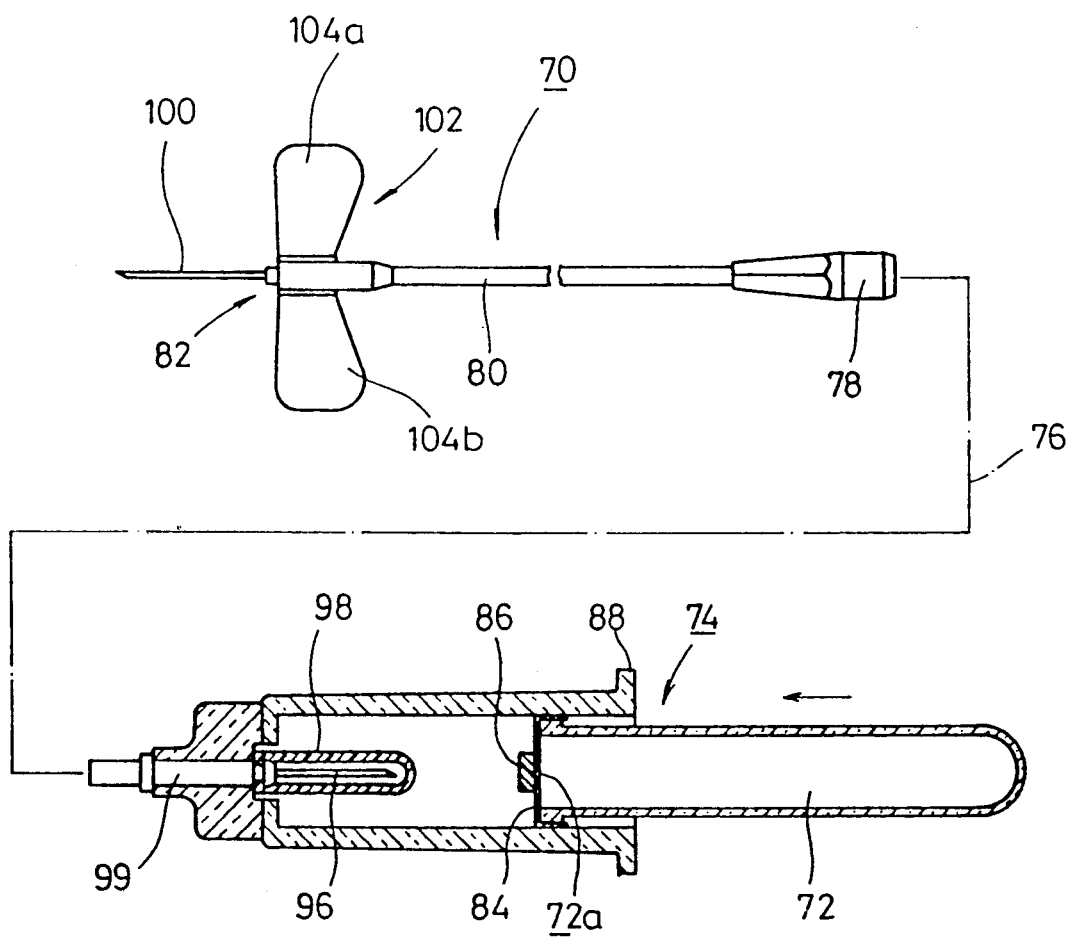
FIG. 5 is a plan view, partly in cross section, of a blood sampling instrument including a blood sample tube holder to be supported by the holder support mechanism shown in FIG. 3.

FIG. 5 shows a blood sampling instrument 70 for use with the blood sample tube stand 30. The blood sampling instrument 70 is basically composed of a transparent evacuated blood sample tube 72 made of synthetic resin and having a hemispherical bottom, a blood sample tube holder 74 in which a distal end portion of the evacuate blood sample tube 72 is fitted, and a winged needle 82 coupled in fluid communicating relation to the blood sample tube holder 74 and an adapter 78 through a tube 80. The evacuated blood sample tube 72 has an open end 72a closed by a cover 84 comprising a thin plate, for example, aluminum foil coated with synthetic resin with elastic member 84 as of rubber being fixed to the center of the cover 84.

Figure 6:
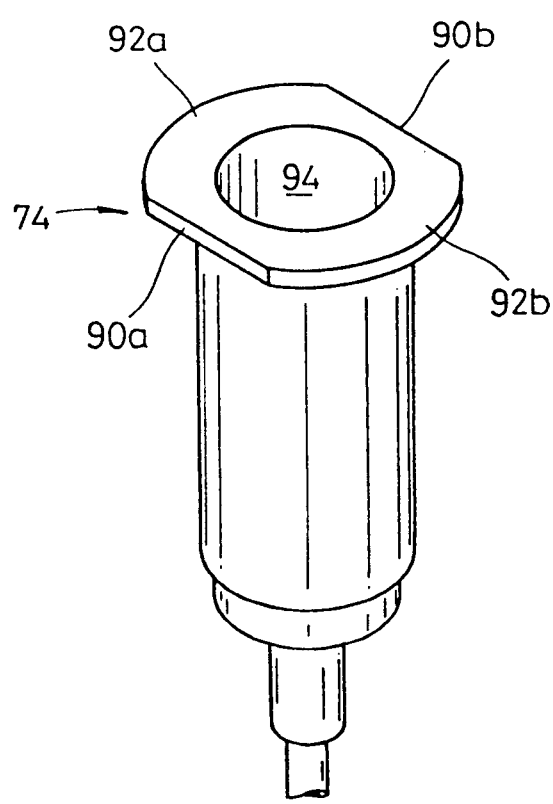
FIG. 6 is a perspective view of the blood sample tube holder shown in FIG. 5.

The blood sample tube holder 74 has a flange 88 on an open end thereof. As shown in FIG. 6, the flange 88 has a pair of diametrically opposed parallel guide surfaces 90a, 90b on its peripheral edge, and a pair of diametrically opposed arcuate edges 92a, 92b between the guide surfaces 90a, 90b. The horizontal walls 55a, 55b of the horizontal support member 46 have portions complementary in shape to the arcuate edges 92a, 92b. The flange 88 has a circular opening 94 defined therein and communicating with the space in the blood sample tube holder 74, for receiving the evacuated blood sample tube 72 therein.

As shown in FIG. 5, a puncture needle 96 is mounted in the blood sample tube holder 74 and has a pointed end directed toward the evacuated blood sample tube 72. The puncture needle 96 is covered with a elastic sheath 98 as of rubber which is relatively soft and can elastically restore its original shape. The puncture needle 96 is held in communication with a communication pipe 99 which is coupled to the tube 76. The winged needle 82 joined to the tube 80 has a cannula 100 and a fixing wing 102 for securing the cannula 100 to a human arm or the like. The fixing wing 102 has a pair of thin fixing wing members 104a, 104b which are spaced apart along a direction perpendicular to the axis of the cannula 100.

The fluid sample tube stand 30 with the holder support mechanism 40 and the blood sampling instrument 70 for use therewith are basically constructed as described above. Operation of the fluid sample tube stand 30, the holder support mechanism 40, and the blood sampling instrument 70 will be described below.

The lower end of the support plate 42 of the holder support mechanism 40 is inserted in the groove 60 in the plate 38, and the step 44 is engaged by the side wall of the stand block 32, thus securely combining the holder support mechanism 40 with the stand block 32. A plurality of evacuated blood sample tubes 72 which are necessary to contain blood samples are inserted in the holes 34, 36. Then, the blood sample tube holder 74 is mounted in the holder support mechanism 40 while the guide surfaces 90a, 90b of the flange 88 are being held against the support arms 48a, 48b, respectively. The arcuate edge 92a of the flange 88 is inserted into the cavity 54 in the horizontal member 46 and prevented from being vertically displaced by the upper and lower walls 55a, 55b of the horizontal member 46. The slanted surfaces 50a, 50b allow the flange 88 to be smoothly inserted into the recess 47. The evacuated blood sample tube 72 is mounted in the blood sample tube holder 74, either beforehand or at this time. More specifically, the open and 72a of the evacuated blood sample tube 72 is inserted into the blood sample tube holder 74 until the elastic member 86 abuts against the tip end of the elastic sheath 98. The evacuated blood sample tube 72 is further inserted, in the direction indicated by the arrow in FIG. 5, to cause the pointed tip of the puncture needle 94 to rupture the elastic member 86. The pointed tip of the puncture needle 94 now penetrates the elastic member 86 and the cover 84, and is inserted into the evacuated blood sample tube 72.

With the blood sample tube holder 74 being thus supported in position by the holder support mechanism 40, the cannula 100 of the winged needle 82 is inserted into a vein in a human body. Alternatively, the cannula 100 may have been inserted in a vein in advance. Then, the fixing wing 102 of the winged needle 82 is securely fastened to the human body by a sticking plaster or an adhesive tape.

Blood then flows from the vein into the evacuated blood sample tube 72 under a vaccum developed therein. When the evacuated blood sample tube 72 is filled with blood, the evacuated blood sample tube 72 is separated from the blood sample tube holder 74. More specifically, the blood sample tube holder 74 is removed from the holder support mechanism 40, and the vaccum blood sample tube 72 is pulled from the blood sample tube holder 74 in the direction opposite to the direction indicated by the arrow in FIG. 5. The puncture needle 96 is removed from the cover 84 and the elastic member 86, and the elastic sheath 98 restores its original shape, covering the pointed tip of the puncture needle 96 again. In the evacuated blood sample tube 72, the opening in the cover 84 which has been produced by the puncture needle 96 is closed and sealed from ambient air by the resilient member 86. The evacuated blood sample tube 72 which has been removed from the blood sample tube holder 74 is inserted in one of the holes 34, 36 in the stand block 32.

The evacuated blood sample tube 72 can easily be inserted into one of the holes 34, 36 which have the tapered surfaces 34a, 36a for smooth slidable contact with the hemispherical bottom of the evacuated blood sample tube 72. The evacuated blood sample tube 72 can be removed from the blood sample tube holder 74 while the latter is being mounted in the holder support mechanism 40. More specifically, since the flange 88 of the blood sample tube holder 74 is inserted in the cavity 54, the upper wall 55a prevents the blood sample tube holder 74 from being displaced upwardly when the evacuated blood sample tube 72 is pulled upwardly from the blood sample tube holder 74. As a result, the evacuated blood sample tube 72 can be removed from the blood sample tube holder 74 even with one hand. Thereafter, another evacuated blood sample tube 72 may be inserted into the blood sample tube holder 74 for collecting another blood sample. In this manner, as many different vaccum blood sample tubes as required may be used with the blood sample tube holder 74.

When all the required evacuated blood sample tubes 72 are held in the stand block 32 and the blood sampling process is finished, the blood sample tube stand 30, with or without the holder support mechanism 40, is sent to an inspection process with the evacuated blood sample tubes 72 being vertically supported by the stand block 32.

Figure 7:
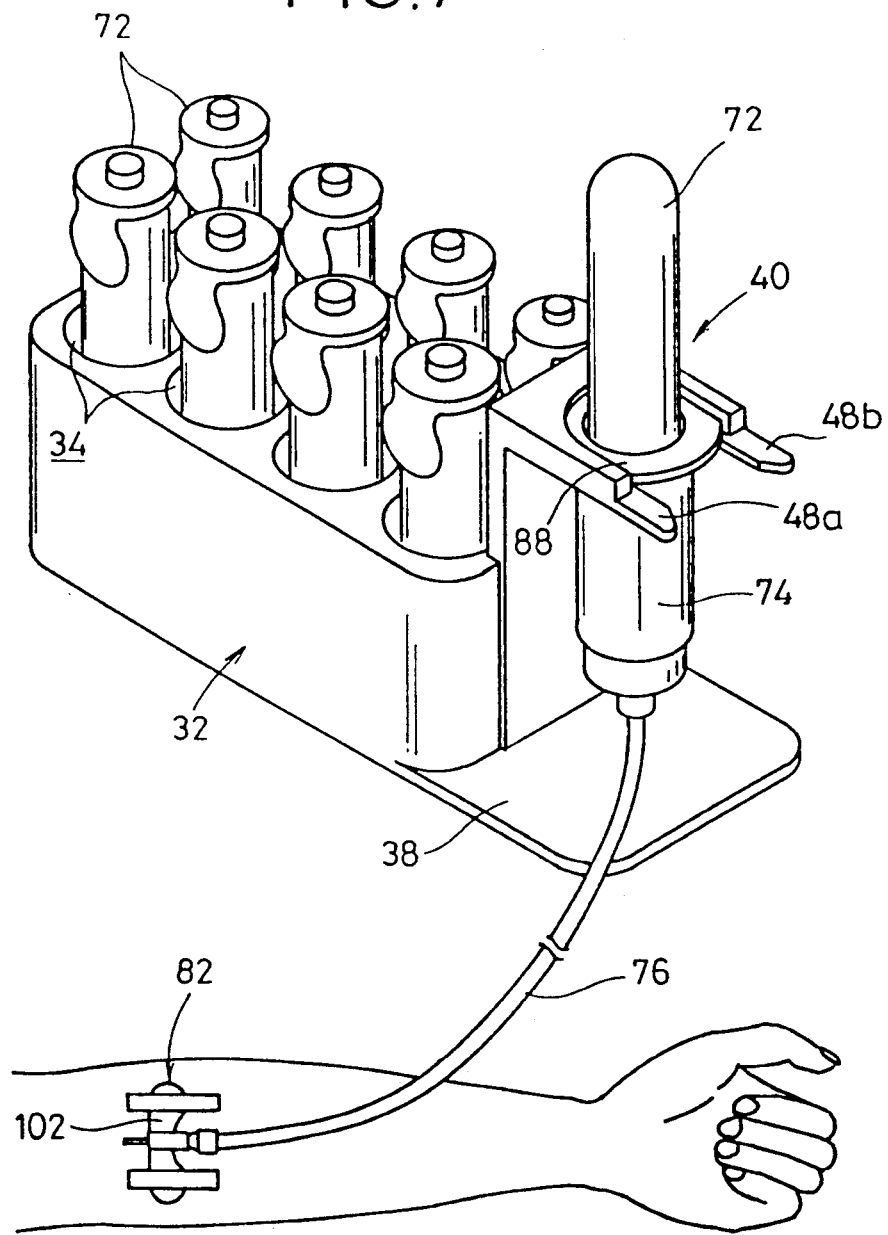
FIG. 7 is a perspective view showing the manner in which the fluid sample tube stand is used to hold blood sample tubes.
Figure 8:
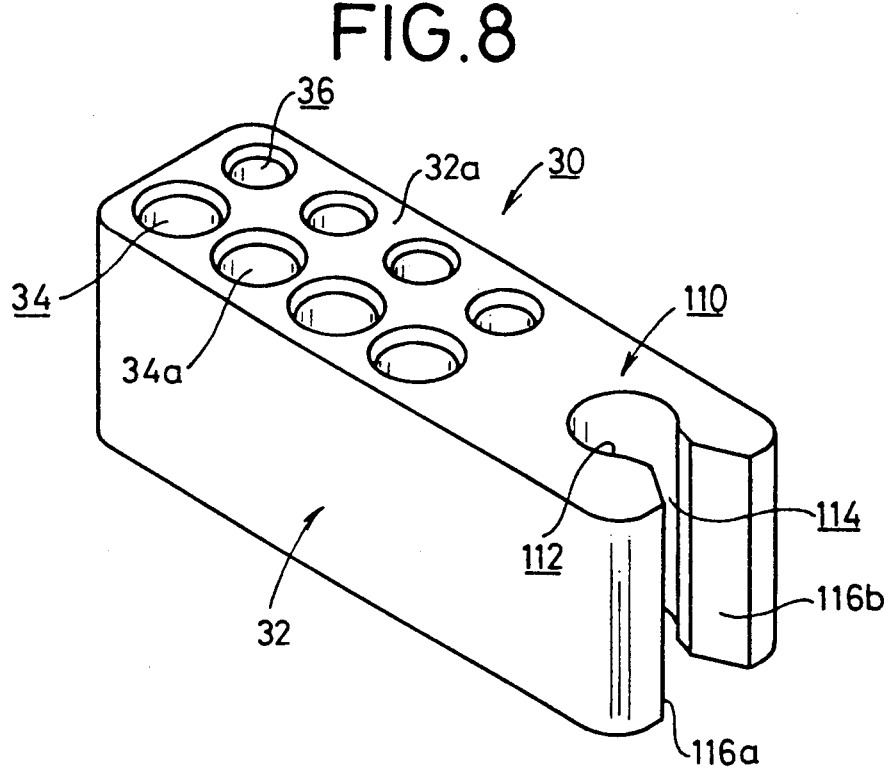
FIG. 8 is a perspective view of a fluid sample tube stand according to another preferred embodiment.
Figure 9:
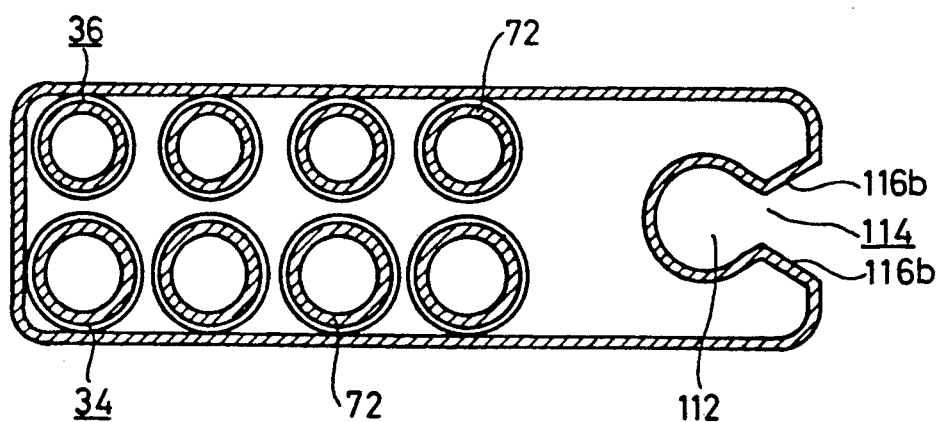
FIG. 9 is a cross-sectional view taken along line 11—11 of FIG. 8.
Figure 10:
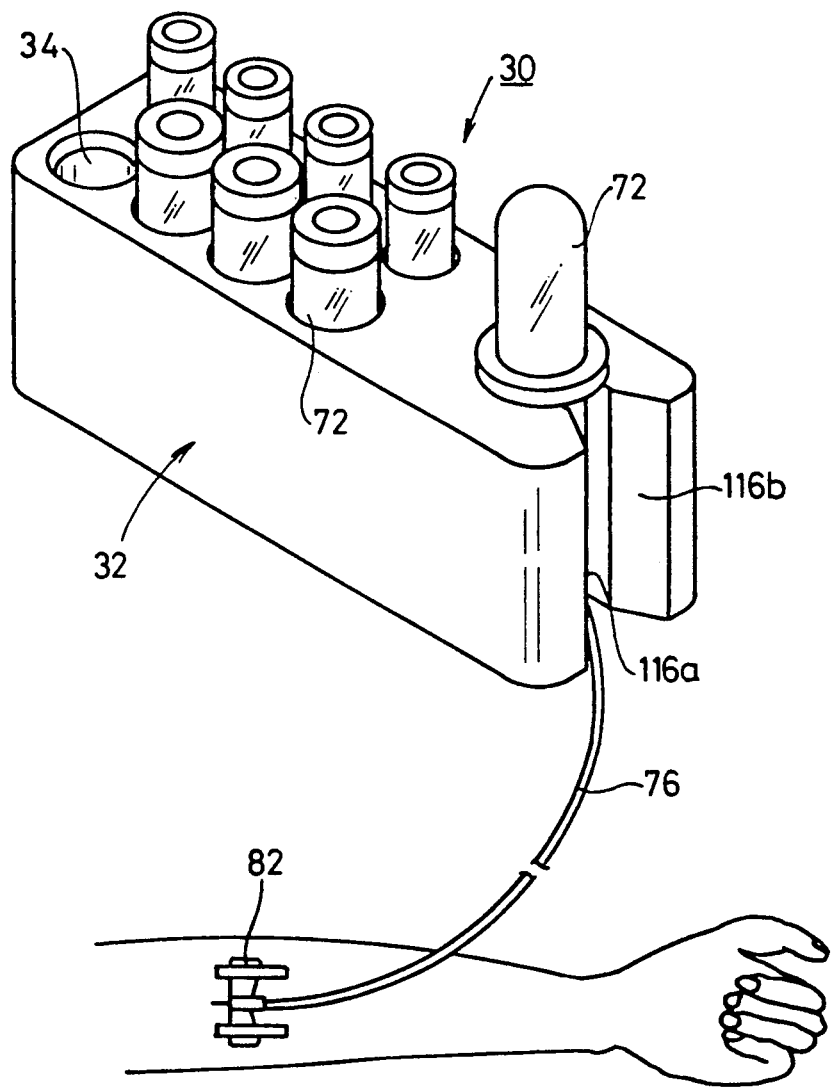
FIG. 10 is a perspective view showing the manner in which the fluid sample tube stand is used to hold blood sample tubes.

FIGS. 8 through 10 illustrate further preferred embodiment of the present invention. In these figures, the same reference numerals to those of FIGS. 1 through 7 denote same elements or members shown in FIGS. 1 through 7 so that detail explanation shall be omitted with regard to those members.

In the present embodiment, a holder support mechanism 110 is in a unitary construction with the stand block 32, which is differently configured to the first embodiment. As is illustrated in FIG. 7, a holder support mechanism 40 is detachably mounted on the stand bock 32.

Actually, the height of the stand block 32 is larger than that of the first embodiment for preventing the tube 76 from being folded when tube holder 74 is held on the holder support mechanism 110.

The holder support mechanism 110 has a holding hole 112 which communicates with a longitudinal opening 114. The opening 114 should be used to pick up the tube 76 of blood sampling instrument 70 and to check a blood sampling operation.

The holder support mechanism 110 has slanted surfaces 116a, 116b at distal and thereof to be elastically spread away each other. These slanted surfaces facilitate for the holder 74 to be held or the holder support mechanism. Thus, plate 38, hole 54 and support arms 48a, 48b of the first preferred embodiment.

According to the embodiment above, the tube 76 is inserted to the hole 112 through the opening 114 and the tube holder 74 is supported at the upper surface of the holder support mechanism 110 as illustrated in FIG. 10. Thus, because of its configuration, the holder support mechanism 110 may not be broken and the blood sample tube stand is prevented from felling down even if the tube 74 is inadvertently hooked on the blood sample tube stand 30.

With the present invention, as described above, the fluid sample tube stand is basically composed of the stand block for holding tubes such as fluid sample tubes and the holder support mechanism for supporting the holder which is detachably mounted on the stand block and which can hold a fluid sample tube. The holder which is combined with a winged needle may be supported by the holder support mechanism, and used in a fluid sampling process. Since one of the hands of the user is free, the user can easily handle the flood sampling instrument. After flood samples have been collected, the fluid sample tubes can successively be vertically held in the stand block. The holes of different diameters defined in the stand block can hold fluid sample tubes of different diameters. This allows the user to easily know the types of the fluid sample tubes and the numbers of the fluid sample tubes which have been filled with fluid samples and are not yet filled with fluid samples.

While the fluid sample tube holder is being mounted in the holder support mechanism, the fluid sample tube which has been filled with a fluid sample can be replaced with an empty fluid sample tube. Therefore, a desired number of blood samples can quickly be collected without fail. The fluid sample tubes which are held in the stand block are prevented from dropping from a table on which the fluid sample tube stand is placed. Even if fluid samples are to be collected from many fluid donors, the fluid samples can be obtained in a short period of time, using the fluid sample tube stand with the holder support mechanism. Inasmuch as the holder support mechanism can easily be detached from the stand block, the fluid sample tube stand can easily be sent to an inspection process or the fluid sample tube stand on the table can easily be simplified for easy subsequent processing of the collected fluid samples.

Although a certain preferred embodiment has been shown and described, it should be understood that many changes and modifications may be made therein without departing from the scope of the appended claims.

What is claimed is:

1. A blood sampling instrument comprising:
   a plurality of evacuated blood sample tubes;
   a holder for holding said evacuated blood sample tubes, one-at-a-time, said holder having an open end into which one of said evacuated blood sample tubes can be inserted, a flange disposed proximate said open end, a puncture needle mounted in a distal end of said holder opposite said open end and projecting into said holder, and a communication passage disposed at said distal end in fluid communication with said puncture needle;
   a blood collection needle held in fluid communication with said communication passage;
   a stand block having a plurality of holes therein for vertically holding said plurality of evacuated blood sample tubes; and
   a holder support mechanism mounted on said stand block for supporting said holder, said holder support mechanism having a pair of support arms coupled to said stand block for supporting said flange of said holder, thereby supporting said holder.

2. A blood sampling instrument according to claim 1, wherein said holder support mechanism include a horizontal support member integral with said support arms, said horizontal support member having a cavity for insertion of said flange therein.

3. A blood sampling instrument according to claim 2, wherein said horizontal support member has arcuate horizontal walls defining said cavity therebetween and having portions complementary in shape to said flange.

4. A blood sampling instrument according to claim 1, wherein said support arms have on distal ends thereof respective slanted surfaces which are spread away from each other.

5. A blood sampling instrument according to claim 1, wherein said holder support mechanism is detachably mounted on said stand block.

6. A blood sampling instrument according to claim 5, wherein said holder support mechanism includes a support plate held against said stand block and a step removably engaging said stand block, whereby said holder support mechanism is detachably mounted on said stand block.

7. A blood sampling instrument according to claim 2, wherein said support arms have on distal ends thereof respective slanted surfaces which are spread away from each other.

8. A blood sampling instrument according to claim 3, wherein said support arms have on distal ends thereof respective slanted surfaces which are spread away from each other.

9. A blood sampling instrument according to claim 1, wherein said blood collection needle comprises a winged needle having a cannula and a pair of fixing wings disposed proximate said cannula.

10. A blood sampling instrument comprising:
    a plurality of evacuated blood sample tubes;
    a holder for holding said evacuated blood sample tubes, one-at-a-time, said holder having an open end into which one of said evacuated blood sample tubes can be inserted, a puncture needle mounted in a distal end of said holder opposite said open end and projecting into said holder, and a communication passage disposed at said distal end in fluid communication with said puncture needle;
    a blood collection needle held in fluid communication with said communication passage;
    a stand block having a plurality of holes therein for vertically holding said plurality of evacuated blood sample tubes; and
    a holder support mechanism for supporting said holder, wherein said holder support mechanism is molded integrally with said stand block as a unitary structure, said holder support mechanism comprising a further hole into which said distal end of said holder can be inserted.

11. A blood sampling instrument according to claim 10, wherein said holder support mechanism includes slanted surfaces at a distal end thereof, said slanted surfaces being spread away from each other, and wherein an opening is defined between said slanted surfaces communicating with said further hole.

12. A blood sampling instrument according to claim 10, wherein said blood collection needle comprises a winged needle having a cannula and a pair of fixing wings disposed proximate said cannula.

* * * * *

UNITED STATES PATENT AND TRADEMARK OFFICE
CERTIFICATE OF CORRECTION

PATENT NO. : 5,127,531

DATED : July 7, 1992

INVENTOR(S) : ONODERA, Tsuneyoshi

It is certified that error appears in the above-identified patent and that said Letters Patent is hereby corrected as shown below:

TITLE PAGE - item   [56] References Cited:

Under "U.S. Patent Documents", right column, insert the following:

| | | |
|---|---|---|
| 3,633,566 | 1/1972 | Grabhorn |
| 3,765,402 | 10/1973 | Grabhorn |
| 4,826,003 | 5/1989 | Levy |
| 4,865,090 | 9/1989 | Burolla et al |
| 4,951,685 | 8/1990 | Blair |
| 4,976,271 | 12/1990 | Blair |

FOREIGN PATENT DOCUMENTS:

| | | |
|---|---|---|
| 0339775 | 11/1989 | Europe |
| 8910764 | 11/1989 | WIPO |

UNITED STATES PATENT AND TRADEMARK OFFICE
CERTIFICATE OF CORRECTION

PATENT NO. : 5,127,531

DATED : July 7, 1992

INVENTOR(S) : ONODERA, Tsuneyoshi

It is certified that error appears in the above-identified patent and that said Letters Patent is hereby corrected as shown below:

```
Column 2, line 30, replace "i to" with --is to--.

Column 2, line 51, replace "enlarges" with --enlarged--.

Column 3, line 50, replace "easily" with --easy--.

Column 6, line 37, replace "felling" with --falling--.
```

Signed and Sealed this

Fifth Day of October, 1993

*Attest:*

BRUCE LEHMAN

*Attesting Officer*     *Commissioner of Patents and Trademarks*